(12) United States Patent
McNeese (10) Patent No.: US 8,657,850 B2
(45) Date of Patent: Feb. 25, 2014

(54) RADIAL ARTERY COMPRESSION DEVICE

(75) Inventor: Marc Anthony McNeese, Caseyville, IL (US)

(73) Assignee: Merit Medical Systems, Inc., South Jordan, UT (US)

( * ) Notice: Subject to any disclaimer, the term of this patent is extended or adjusted under 35 U.S.C. 154(b) by 427 days.

(21) Appl. No.: 12/349,405

(22) Filed: Jan. 6, 2009

(65) Prior Publication Data

US 2009/0281565 A1 Nov. 12, 2009

Related U.S. Application Data

(60) Provisional application No. 61/050,907, filed on May 6, 2008.

(51) Int. Cl.
*A61B 17/00* (2006.01)

(52) U.S. Cl.
USPC .......................................... 606/201; 600/490

(58) Field of Classification Search
USPC .......... 606/201–204, 157, 158, 213; 600/490,
600/499; 601/134, 135, 151, 152; 24/486,
24/569; 251/8; 128/112.1, 106.1
See application file for complete search history.

(56) References Cited

U.S. PATENT DOCUMENTS

| | | | | |
|---|---|---|---|---|
| 1,281,653 | A | * | 10/1918 | Plummer ....................... 606/203 |
| 2,332,107 | A | | 10/1943 | Nieburgs |
| 3,050,064 | A | | 8/1962 | Moore et al. |
| 3,376,846 | A | | 4/1968 | Sekiguchi et al. |
| 4,307,799 | A | | 12/1981 | Zouzoulas |
| 4,479,495 | A | * | 10/1984 | Isaacson ....................... 606/204 |
| 4,557,262 | A | * | 12/1985 | Snow ........................... 606/201 |

(Continued)

FOREIGN PATENT DOCUMENTS

| | | |
|---|---|---|
| CN | 201205292 | 3/2009 |
| DE | 4006696 A | 11/1990 |
| FR | 2828231 A | 2/2003 |
| WO | WO2004/041313 | 5/2004 |

OTHER PUBLICATIONS

Notification of Transmittal of the International Search Report and the Written Opinion of the International Searching Authority issued Nov. 18, 2009 in International Application No. PCT/US2009/042868.

(Continued)

*Primary Examiner* — Katherine Dowe
*Assistant Examiner* — Katrina Stransky
(74) *Attorney, Agent, or Firm* — Stoel Rives LLP (57) ABSTRACT

A radial artery compression device configured to be releasably secured by a strap or band to the underside of a wrist of a patient and to provide adjustable and consistent compression pressure in the area of a radial artery access site to achieve hemostasis either during or after a medical procedure such as a percutaneous coronary procedure. The radial artery compression device includes a body configured to engage and secure a knob while allowing the knob to rotate with respect to the body. Rotation of the knob can cause a threaded shaft to move. The threaded shaft mechanically couples the knob to a disk-shaped compression pad. The compression pad can include one or more notches adapted to at least partially surround a sheath and/or a catheter inserted into the radial artery at the access site. The compression pad can also include a step on the surface to provide a desired amount of contour to a portion of a device within the radial artery during a procedure.

19 Claims, 6 Drawing Sheets

(56) References Cited

U.S. PATENT DOCUMENTS

| | | | |
|---|---|---|---|
| 5,139,512 A | 8/1992 | Dreiling et al. | |
| 5,269,803 A * | 12/1993 | Geary et al. | 606/201 |
| 5,304,186 A * | 4/1994 | Semler et al. | 606/151 |
| 5,304,201 A * | 4/1994 | Rice | 606/201 |
| 5,728,120 A * | 3/1998 | Shani et al. | 606/201 |
| 6,068,646 A * | 5/2000 | Lam | 606/203 |
| 6,833,001 B1 * | 12/2004 | Chao | 606/203 |
| 7,780,612 B2 * | 8/2010 | Ross | 602/5 |
| 2003/0055453 A1 * | 3/2003 | Akerfeldt | 606/203 |
| 2005/0113866 A1 | 5/2005 | Heinz et al. | |
| 2005/0125025 A1 * | 6/2005 | Rioux | 606/201 |
| 2006/0058841 A1 | 3/2006 | Mills et al. | |
| 2007/0239092 A1 * | 10/2007 | Ross | 602/20 |
| 2010/0280541 A1 | 11/2010 | Lampropoulos | |

OTHER PUBLICATIONS

Medplus, Inc., "Tourniquet (Radial Artery Compression Device)", http://www.bikudo.com/product_search/details/187473/tourniquet_radial_artery_compression_device.html, Nov. 24, 2009.

Notice of Allowance dated Oct. 16, 2012 for U.S. Appl. No. 12/435,227.

Office Action dated Mar. 5, 2013 for U.S. Appl. No. 13/741,046.

* cited by examiner

RADIAL ARTERY COMPRESSION DEVICE

CROSS REFERENCE TO RELATED APPLICATIONS

This application claims the benefit of priority to U.S. Provisional Patent Application No. 61/050,907, filed on May 6, 2008, entitled "Pressurized Blood Flow Occlusion Device," the entire contents of which are incorporated herein by reference.

BACKGROUND OF THE INVENTION

1. Field of the Invention

The present disclosure relates to a radial artery compression device. In more particular, the present disclosure relates to a radial artery compression device configured to be releasably secured to the wrist of a patient and to provide an adjustable level of compression pressure on the radial artery to achieve hemostasis at, or in the area of, a vascular access site.

2. Relevant Technology

Medical advancements have resulted in the ability to diagnose and treat coronary artery disease using vascular delivery apparatus and techniques. One advantage of coronary procedures utilizing vascular delivery is that a practitioner can access a desired position within the patient's body without administering general anesthetic or requiring highly invasive surgery. During a typical procedure, a sheath having a haemostatic valve is utilized to access a peripheral artery utilizing the administration of a local anesthetic at the vascular access site. A pre-shaped catheter is then introduced into the patient's vasculature through the sheath. The catheter can then be advanced to the ostium of the relevant coronary artery or to another desired location within the patient. The catheter enables delivery of medical instruments, medicines or fluids such as radiography contrast medium, angioplasty wires, balloons, and stents. During or after completion of the procedure, the sheath and catheter are removed and hemostasis can be achieved by manual compression, suturing the access site, or by utilizing another direct repair procedure.

Often these percutaneous coronary diagnostic and interventional procedures are accomplished through the radial artery of a patient. Radial artery access has the potential advantages of reduced access site complications, rapid patient mobilization, and reduced costs. The relatively superficial position of the distal radial artery enables relatively direct application of compression to the artery to achieve and maintain hemostasis during a procedure. Additionally the radial artery allows quick and direct closure at the catheter access site as soon as the arterial catheter has been removed at the end of the procedure.

As with any arterial puncture, achieving hemostasis during and/or after a procedure can be challenging. Typically the access site, or opening, in the artery is created utilizing a micropuncture apparatus, dilator or can even be formed utilizing a single straight incision to form a slit in the artery. The arterial walls include a layer of smooth muscle cells that expand and contract in conjunction with the rhythm of the heart to complement the pumping of the heart and to facilitate movement of blood throughout the body. The expanding and contracting of the radial artery may present challenges to achieving hemostasis at the access site. As a result of this and other factors, during the course of the procedure, blood may leak through the access site and around the outside diameter of the sheath or catheter. Existing radial artery compression devices are not adapted to provide desired and/or adjustable compression to the radial artery at the vascular access site during the course of a procedure.

When the procedure has been completed, typically the catheter is removed and the practitioner or medical professional will apply pressure at the vascular access site to achieve hemostasis and effectuate closure of the vascular access site. One technique for achieving hemostasis is to apply pressure at, or at a point slightly upstream, of the vascular access site. Typically, continuous pressure is necessary to stop bleeding and achieve hemostasis at the access site. While the applied pressure should remain relatively constant, there are advantages to applying a higher level of compression pressure at the beginning of the compression period and then reducing the level of compression pressure after a determined amount of time has elapsed. By gradually reducing the compression pressurization during the compression period, while continually maintaining at least a threshold level of compression, blood can begin to flow through the artery at a reduced pressure, providing nutrient rich blood to the tissue downstream from the access site. Blood flowing through the artery can then hasten clotting to enable hemostasis without application of ongoing compression. Not only can this provide improved closure, but also can improve the relative comfort of the patient.

Compression is typically applied to an access site by a nurse or other practitioner by manually holding a dressing at the access site. Although employing a practitioner to provide compression permits the gradual reduction of pressurization at the access site, it can also be a costly use of practitioner time. Alternative existing radial artery compression techniques which do not require the ongoing manual application of pressure by the practitioner may employ tape or a compression bandage at the vascular access site. These devices and techniques, while allowing the practitioner to attend to other matters, can render it difficult or impractical to adjust the compression pressure while maintaining continuous pressure. As a result, the tape or compression bandages may end up being positioned around the access site without being loosened or adjusted until they are removed.

BRIEF SUMMARY OF THE INVENTION

The present invention relates to a radial artery compression device configured to be releasably secured by a strap or band to the underside of a wrist of a patient to provide continuous and adjustable compression in the area of a radial artery access site. The radial artery access site can be an opening formed utilizing a micropuncture apparatus, a dilator, an incision, or other percutaneous access device or procedure which allows insertion of a sheath and/or a catheter into the radial artery. The radial artery compression device can be configured to provide compression pressure in the area of the radial artery access site to achieve hemostasis. The radial artery compression device of the present invention is effective for achieving hemostasis at the access site during and after a medical procedure such as a vascular delivery procedure.

According to one embodiment, the radial artery compression device includes a body configured to engage and secure a knob while allowing the knob to rotate with respect to the body of the radial artery compression device. As the knob is rotated, female threads of the knob engage a threaded shaft and cause the threaded shaft to move. The threaded shaft can be coupled to a compression pad formed of rigid material and shaped like a disk. As the shaft moves, the compression pad is either extended away from the body of the device or retracted toward the body of the device, depending on the direction the knob is rotated. According to another aspect of the present invention, the compression pad can include one or more notches adapted to at least partially surround a sheath and/or a catheter inserted into the radial artery at the access site. The compression pad can also include a step on the surface, or can otherwise be configured, to at least partially contour to a portion of a sheath and/or a catheter within the radial artery during a procedure. The radial artery compression device can further comprise a band coupled to the body and configured to secure the body to the underside of a wrist of a patient in the area of the radial artery.

According to another embodiment, the threaded shaft is coupled to the knob, and rotates as the knob is rotated. The shaft mates with threads on the compression pad. As the shaft rotates, the compression pad is either extended away from the body of the device or retracted toward the body of the device, depending on the direction the knob is rotated.

DETAILED DESCRIPTION

Percutaneous coronary diagnostic and interventional procedures can be performed through a catheter introduced into the radial artery. A sheath with a hemostatic valve is inserted into an opening, or access site, into the radial artery. A preshaped catheter can then be passed through the sheath to the ostium of the relevant coronary artery or other position within the patient's body. The catheter enables delivery of instruments and fluids such as contrast medium, angioplasty wires, balloons, and stents. During the procedure, maintaining hemostasis at the access site is desirable to reduce the patient's loss of blood, allow for desired performance during the procedure and limit risk of infection. After completion of the procedure, the sheath and catheter are removed and the flow of blood through the access site is stopped.

As with any arterial puncture, achieving hemostasis during and after a procedure can be challenging. During the procedure, blood may leak around the sheath or catheter through the opening. Typically the access site, or opening, in the artery is created utilizing a micropuncture device, a dilator, or a single straight incision to form a slit. The access site may not conform closely to the tubular-shaped sheath and catheter. Moreover, the arterial walls include a layer of smooth muscle cells that expand and contract in conjunction with the rhythm of the heart to complement the pumping of the heart and move blood throughout the body. The expanding and contracting of the radial artery can present challenges to achieving hemostasis at the access site during a procedure. Additionally, the nature of vascular catheter access can make it difficult to achieve hemostasis when the catheter is positioned within the radial artery. This is because the practitioner is providing pressurization on the radial artery when the catheter is positioned within the artery. After the procedure has been completed and the catheter has been removed, the size of the catheter access bore, and movement of the patient's arm and/or wrist may cause stretching and contraction of the tissue surrounding the access site and can prevent clotting and thereby delay hemostasis.

The present invention is directed to a radial artery compression device that can be releasably secured to the underside of a wrist of a patient and provide adjustable compression pressurization in the area of a radial artery access site. The radial artery compression device is configured to provide consistent and adjustable compression pressure in the area of the radial artery access site to achieve hemostasis. The radial artery compression device disclosed is adapted to achieve hemostasis at the access site both during and after the completion of a percutaneous coronary procedure.

According to one embodiment, the radial artery compression device includes a body configured to engage and secure a knob while allowing the knob to rotate with respect to the body. As the knob is rotated, female threads of the knob engage a threaded shaft and cause the threaded shaft to move. The threaded shaft can be formed of rigid material and coupled to a compression pad. The compression pad can be formed of rigid or flexible material and shaped like a disk. The compression pad can be advanced such that the pad is extended away from the body of the device to provide additional compression. The compression pad can also be retracted toward the body of the device to provide a lesser amount of compression or to remove compression entirely.

According to another aspect of the present invention, the compression pad can include one or more notches positioned on the outer periphery of the compression pad. The notches can be adapted to at least partially conform to and/or at least partially surround a sheath and/or a catheter inserted into the radial artery at the access site. The compression pad can also include a step on the surface, or otherwise be configured, to at least partially conform to a portion of a sheath and/or a catheter within the radial artery during a procedure. The radial artery compression device can further comprise a band coupled to the body and configured to secure the body to the underside of a wrist of a patient in the area of the radial artery.

According to another embodiment, the threaded shaft is coupled to the knob, and rotates as the knob is rotated. The shaft mates with female threads on the compression pad. As the shaft rotates, the compression pad is either extended away from the body of the device or retracted toward the body of the device, depending on the direction the knob and shaft are rotated.

Figure 1:
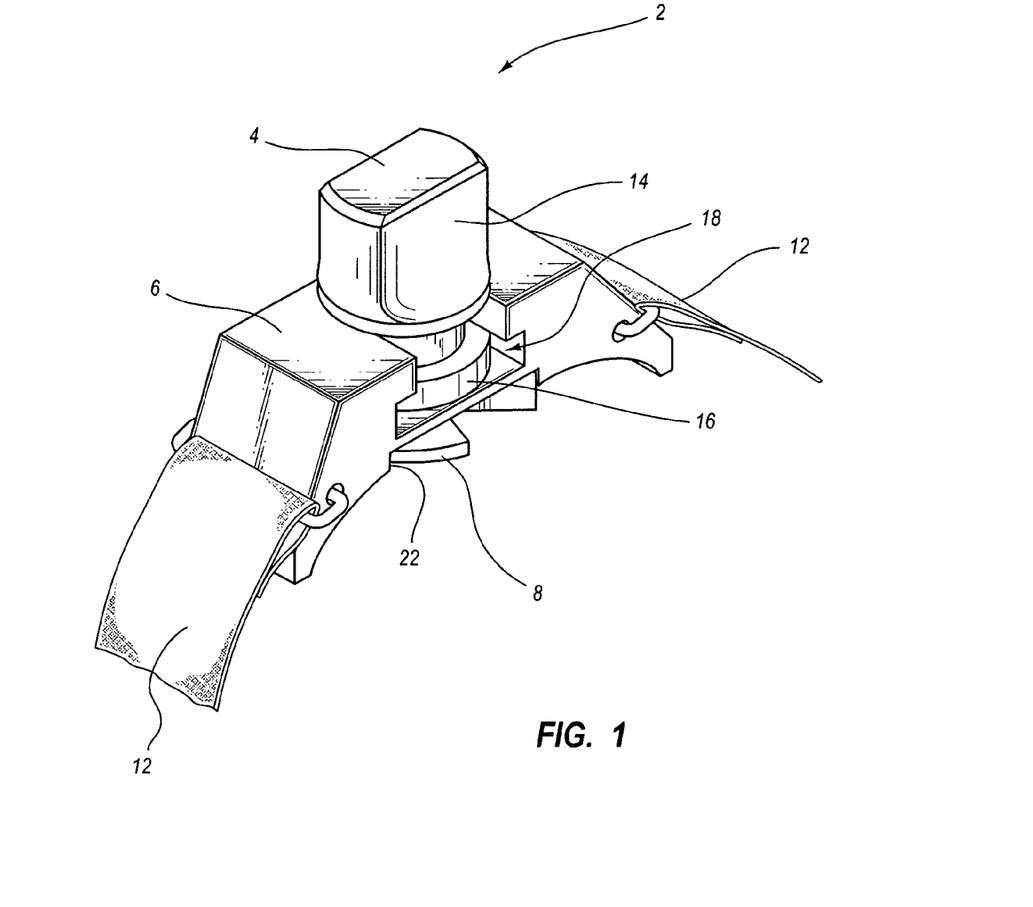
FIG. 1 is a front perspective view of a radial artery compression device.
Figure 2:
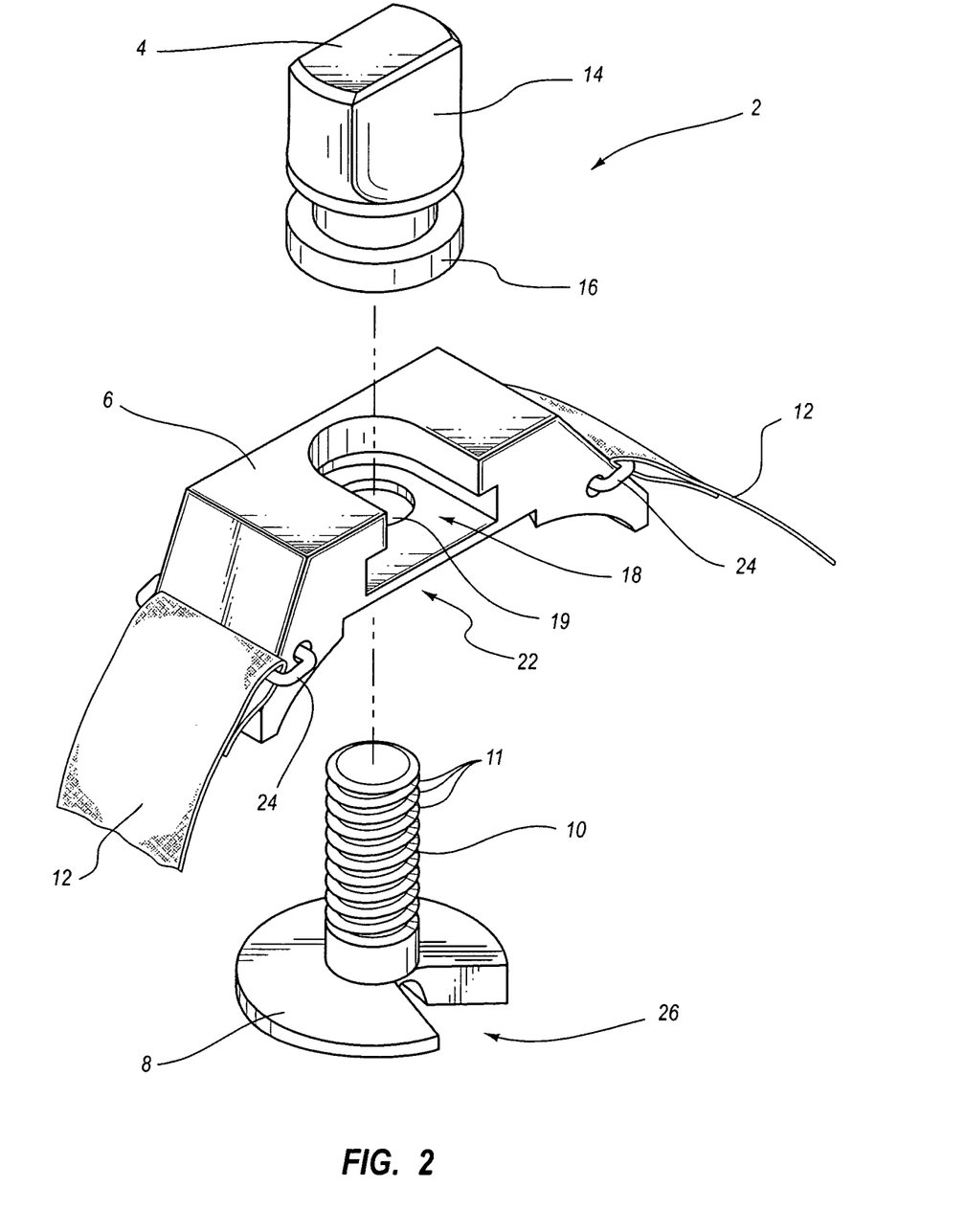
FIG. 2 is an partial exploded component view of a radial artery compression device.

FIG. 1 is a perspective view of a radial artery compression device 2. FIG. 2 is an exploded view of radial artery compression device 2 of FIG. 1. Radial artery compression device 2 comprises a knob 4, a body 6, a compression pad 8, a threaded shaft 10, and a wrist strap 12. Radial artery compression device 2 is configured to be strapped to a wrist of a patient utilizing wrist strap 12. Radial artery compression device 2 is strapped to the wrist of the patient in a manner that positions body 6 on the underside of the patient's wrist with compression pad 8 positioned adjacent the patient's wrist. Threaded shaft 10 is disposed through body 6 to mechanically couple compression pad 8 and knob 4. As knob 4 is rotated, threads 5 (see FIGS. 4A and 4B) on an inside diameter of knob 4 engage threads 11 of threaded shaft 10 and cause threaded shaft 10 to move relative to body 6. Compression pad 8 is coupled to threaded shaft 10 such that as threaded shaft 10 is rotated by interaction with knob 4, compression pad 8 is displaced relative to body 6. Depending on the rotational direction knob 4 is rotated, compression pad 8 moves further from body 6 or closer to body 6. In this manner, additional compression can be applied to or removed from a radial artery of a patient when radial artery compression device 2 is properly secured to the patient's wrist. Moreover, the compression pressurization can be increased or decreased as desired without removing radial artery compression device 2 from the wrist of the patient.

Body 6 can be configured to support knob 4, threaded shaft 10, compression pad 8, and wrist strap 12. Body 6 includes an opening 19 through which threaded shaft 10 can be disposed. Knob 4 is configured to engage threads at one end of threaded shaft 10 while threaded shaft 10 is disposed through opening 19. Knob 4 is positioned on the outward facing extent of body 6. The outward facing extent of body 6 is configured to face away from a wrist of a patient when radial artery compression device 2 is secured to the wrist of the patient. Compression pad 8 couples to the other end of threaded shaft 10 which is positioned on the opposing side of body 6 such that compression pad 8 is positioned adjacent to the wrist of the patient when radial artery compression device 2 is secured to the wrist of the patient.

Body 6 includes a recess 22 on the underside of body 6 to receive compression pad 8 when compression pad 8 is in a retracted position adjacent body 6. Body 6 can further comprise rings 24 to enable coupling of wrist strap 12 to body 6. In one illustrative embodiment, wrist strap 12 comprises a two-piece band, similar to a two-piece watch band. In one embodiment, radial artery compression device 2 is secured to the patient utilizing Velcro straps. To reduce potential discomfort to a patient, body 6 can also be configured to at least partially contour to the underside of a wrist of the patient so as to abut the patient's wrist in a comfortable and ergonomic manner.

In the illustrated embodiment, body 6 comprises an aperture 18 configured to secure knob 4 in a fixed position along the axis of rotation of knob 4. Aperture 18 receives and secures a collar 16 of knob 4 such that knob 4 can freely rotate with respect to body 6 about the axis of rotation of knob 4, while limiting displacement longitudinally along the axis of rotation. Due to the fact that body 6 secures knob 4 from longitudinal displacement along the axis of rotation, compression pad 8 and threaded shaft 10 are displaced relative to body 6 along the axis of rotation of knob 4 as knob 4 rotates. In this manner the level of compression pressure can be adjustably increased or decreased by rotation of knob 4 when radial artery compression device 2 is secured to the wrist of a patient.

Knob 4 can include threads (see e.g. FIGS. 4A and 4B) configured to engage threaded shaft 10. As knob 4 rotates, the threads of knob 4 displace threaded shaft 10 longitudinally along the axis of rotation of knob 4. Knob 4 can further include a finger grip portion 14 which provides an ergonomic surface facilitating grasping and manipulation of knob 4 allowing a user to simply and efficiently rotate knob 4 relative to body 6. As previously discussed, knob 4 can further comprise a collar 16 which facilitates the rotation of knob 4 relative to body 6. Collar 16 can also be configured to be secured by body 6 to restrict unintended displacement of knob 4 relative to body 6. Body 6 is configured to engage at least a portion of knob 4 in a manner that allows knob 4 to freely rotate about the axis of rotation of threaded shaft 10 without being displaced longitudinally or otherwise being removed from body 6.

FIG. 2 depicts an exploded view of radial artery compression device 2. In the illustrated embodiment, collar 16 of knob 4 and aperture 18 of body 6 are illustrated. Collar 16 can be received into a side opening of aperture 18 provided on the lateral extent of body 6. Body 6 is designed such that the upper surface of collar 16 is in contact with the downward facing surface of aperture 18. In this manner, in the event that upward forces are exerted on knob 6, interaction between the upper surface of collar 16 and downward facing surface of aperture 18 will retain the position of knob 4 relative to body 6. Additionally, in the event that downward forces are exerted on knob 6, the bottom surface of collar 16 is engaged by the upward facing surface of aperture 18. In this manner, the position of knob 4 relative to body 6 is maintained. Prior to the threads of knob 4 engaging threaded shaft 10, knob 4 may be movable in a lateral direction with respect to body 6. However, once the threads of knob 4 engage threaded shaft 10 lateral movement of knob 4 is restricted due to securement of threaded shaft 10 by body 6.

Threaded shaft 10 is disposed through opening 19 of body 6 providing a linkage between knob 4 and compression pad 8. Threaded shaft 10 can be formed of a rigid, semi-rigid, or flexible material, such as for example plastic, wood, metal or other suitable materials. Threaded shaft 10 includes threads 11 on at least a portion of threaded shaft 10. Threads 11 provide cooperative engagement with threads on body 6 and/or knob 6 to enable longitudinal displacement of threaded shaft 10. Opening 19 is configured to secure threaded shaft 10, restricting movement of threaded shaft 10 in a lateral direction while allowing threaded shaft 10 to move longitudinally. As knob 4 is rotated, threaded shaft 10 can move longitudinally through body 6 to extend compression pad 8 away from body 6 or retract compression pad 8 closer to body 6. Longitudinal movement of threaded shaft 10 adjusts the pressure applied by compression pad 8 to the wrist and/or radial artery of a patient when radial artery compression device 2 is secured to the underside of a wrist of the patient.

Knob 4 is an example of means for rotating a plurality of threads. A compression pad is an example of means for compressing a radial artery of a patient. A compression pad coupled to a threaded shaft is another example of means for compressing a radial artery of a patient. A body is an example of a means for supporting a rotating means and a compressing means. A band is an example of means for securing a supporting means to a wrist of a patient. A notch in a compression pad is an example of means for at least partially surrounding a device inserted into a radial artery of a patient. A step on a surface of a compression pad configured to be positioned adjacent a wrist of a patient is an example of means for at least partially contouring to a device inserted into a radial artery of a patient.

Figure 3:
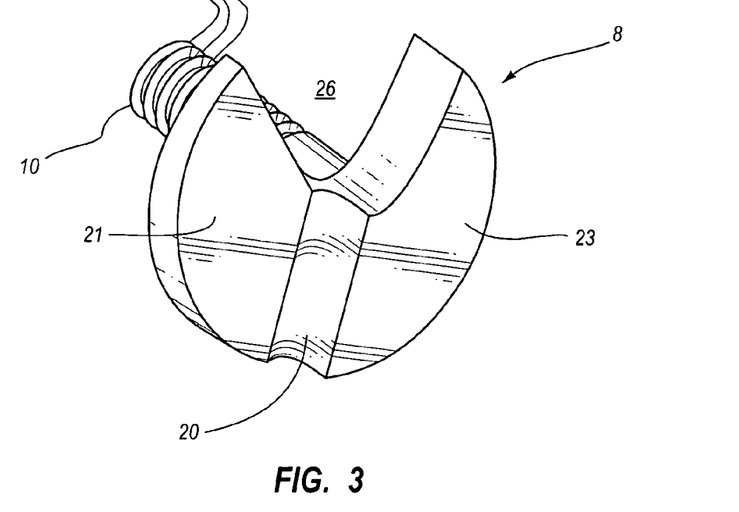
FIG. 3 is a bottom view of a compression pad of the radial artery compression device of FIG. 1.

FIG. 3 is a bottom perspective view of a compression pad 8 of the radial artery compression device 2 of FIG. 1. The surface of body 6 can be configured to partially contour to the underside of a wrist of a patient. The bottom view of FIG. 3 also depicts the surface of compression pad 8 configured to be positioned over, or in the area of, the radial artery on the underside of the wrist of the patient. In the illustrated embodiment, compression pad 8 is coupled to threaded shaft 10. Accordingly, longitudinal movement of threaded shaft 10 results in movement of compression pad 8 relative to body 6. Compression pad 8 includes a curved step 20, a first contact surface 21 and a second contact surface 23. First contact surface 21 has a first elevation and second contact surface 23 has a second elevation that is different from the elevation of first contact surface 23. Curved step 20 provides a transition from first contact surface 21 to second contact surface 23. In the illustrated embodiment, curved step 20 has a radius that approximates the outer diameter of illustrative catheters and/or sheaths that can be positioned in the radial artery.

The profile of first contact surface 21, second contact surface 23 and curved step 20 provides a desired contact with the contours of a patient's wrist. The lower elevation of first contact surface 21 is adapted to conform to the generally raised profile of the center of a patient's wrist. The higher elevation of the second contact surface 23 is adapted to conform to the generally depressed or sloped shape of the portion of the patient's wrist positioned laterally to the radial artery. Curved step 20 enables compression pad 8 to at least partially contour to a portion of a sheath or catheter inserted into the radial artery of a patient. The ability to contour to a sheath or catheter inserted into the radial artery allows radial artery compression device 2 to be positioned such that compression pad 8 can apply compression pressure during a medical procedure. The juxtaposition of first contact surface 21, second contact surface 23 and curved step 20 not only conform to the physiological features of a patient's wrist, but also provide reliable and slip free engagement of the radial artery and surrounding tissues during potentially prolonged use of the device. Utilizing radial artery compression device 2 during a procedure to apply compression pressure can facilitate safe and reliable hemostasis at the access site of the radial artery.

In the illustrated embodiment compression pad 8 is substantially disc-shaped. Compression pad 8 can further comprise a notch 26 formed in the outer perimeter of the compression pad 8. Notch 26 is configured to at least partially contour to a sheath or catheter inserted into the radial artery at an access site. By contouring to an inserted sheath or catheter, notch 26 facilitates application of pressure at an access site during a medical procedure. Compression pad 8 can be positioned upstream to the access site and notch 26 can be positioned to partially surround an inserted sheath or catheter to enable application of compression pressure and thereby facilitate hemostasis at the access site.

Figure 4A:
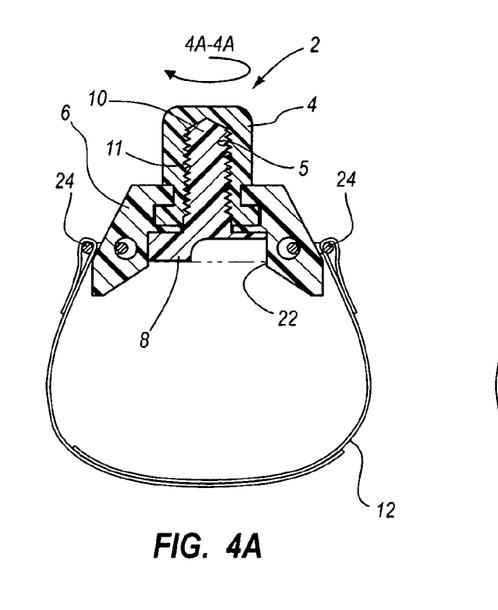
FIG. 4A is a cross-sectional side view of a radial artery compression device illustrating the compression pad in a fully retracted position.

FIG. 4A is a cross-sectional side view of radial artery compression device 2 depicting a configuration in which compression pad 8 is fully retracted toward body 6. In the illustrated embodiment of FIG. 4A, a practitioner rotates knob 4 in a clockwise direction, as indicated by directional arrow 4A-4A, to retract compression pad 8 and threaded shaft 10 toward body 6. When fully retracted, compression pad 8 is received into recess 22 of body 6. In the fully retracted position shown in FIG. 4A, compression pad 8 can be completely contained within recess 22, and thus minimize compression pressure to an access site. Accordingly, a practitioner may opt to secure radial artery compression device 2 to the wrist of a patient while compression pad 8 is in the fully retracted position so that initially no compression pressure is applied to the access site.

Figure 4B:
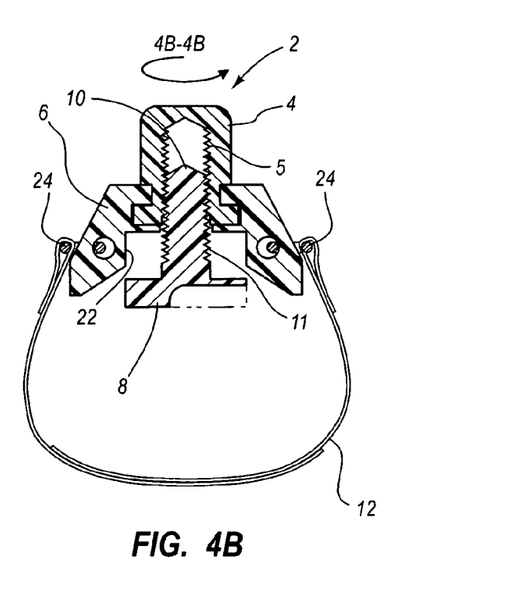
FIG. 4B is a cross-sectional side view of a radial artery compression device illustrating the compression pad in an extended configuration.

FIG. 4B is a cross-sectional side view of radial artery compression device 2 in which compression pad 8 is extended away from body 6. In the illustrated embodiment, knob 4 is rotated in a counterclockwise direction, illustrated by directional arrow 4B-4B, to move the threaded shaft 10 and compression pad 8 away from body 6. When radial artery compression device 2 is secured to the underside of a wrist of a patient, counterclockwise rotation of knob 4 moves compression pad 8 toward the wrist of the patient and provides the ability to apply incrementally increasing amounts of pressure at the radial artery compression site. When radial artery compression device 2 is properly positioned over the radial artery, the compression pressure is applied to the radial artery. Knob 4 can continue to be rotated in a counterclockwise direction to increase the amount of compression pressurization around the access site to achieve a desired level of hemostasis. Similarly knob 4 can be rotated clockwise to decrease the amount of compression pressurization. In this manner, a practitioner can adjust the amount of pressure to achieve a desired level of hemostasis at the access site while maintaining relative comfort of the patient.

Figure 5:
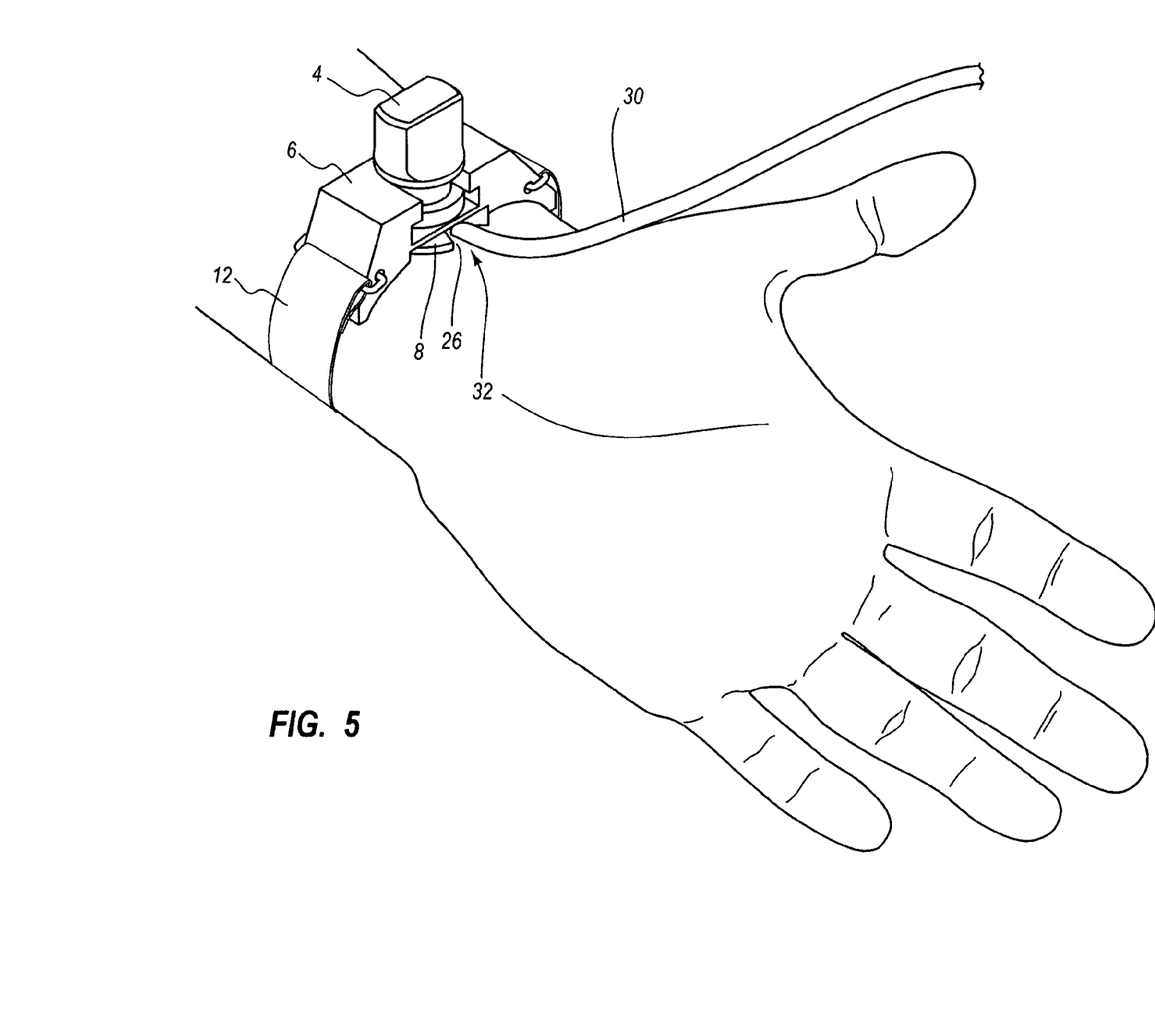
FIG. 5 is a perspective view of a radial artery compression device positioned on the underside of a patient's wrist such that the device can provide compression to the radial artery.

FIG. 5 is a perspective view of a radial artery compression device 2 positioned on the underside of a patient's wrist over the radial artery. Wrist strap 12 secures body 6 to the wrist of the patient. Compression pad 8 of radial artery compression device 2 is positioned in the area of the radial artery of the patient, which is on the underside of the patient's wrist slightly off center toward the thumb side of wrist. In the illustrated embodiment, a catheter 30 is inserted into the radial artery at an access site 32. Compression pad 8 is positioned over the radial artery in the area of access site 32. Notch 26 of compression pad 8 can be positioned adjacent to and partially surrounding catheter 30. In this manner, compression can be applied in the area of access site 32 during the medical procedure to facilitate hemostasis at access site 32. A practitioner can rotate knob 4 counterclockwise to increase the level of pressure to achieve hemostasis. The practitioner can also rotate knob 4 in a clockwise direction to decrease compression pressurization as needed to maintain relative comfort of the patient.

After the medical procedure is complete, radial artery compression device 2 enables a practitioner to remove catheter 30 from the radial artery of the patient without removing radial artery compression device 2 from the wrist of the patient. The practitioner can rotate knob 4 to a desired clockwise displacement to sufficiently reduce compression pressurization to allow removal of catheter 30 from access site 32. After catheter 30 is completely withdrawn from access site 32, radial artery compression device 2 remains advantageously positioned to allow quick and efficient application of compression to access site 32. The practitioner can quickly rotate knob 4 to increase compression pressure applied by compression pad 8 and quickly achieve a desired level of hemostasis. Because radial artery compression device 2 enables rapid application of compression, blood loss of the patient is reduced, risks of transfer of blood-borne diseases is reduced, and closure of the access site can begin immediately. Additionally, the practitioner can apply continued pressurization in a hands free manner allowing the practitioner to attend to other aspects of the procedure until an adjustment of pressurization is to be effectuated. In this manner, radial artery compression device 2 can be utilized both during and after a medical procedure to apply compression pressure to achieve hemostasis.

A similar process can be utilized to remove a sheath from the radial artery after a catheter has been properly inserted. Traditionally, a sheath is first inserted into the radial artery at the access site and then a catheter is inserted through the sheath to perform the percutaneous diagnostic or interventional medical procedure. The practitioner can use radial artery compression device 2 to achieve hemostasis once the sheath is inserted. The catheter can then be inserted through the sheath. In some instances the sheath is removed after the catheter is inserted. Radial artery compression device 2 allows the practitioner to briefly reduce compression pressure at the access site to allow the sheath to be removed. After the sheath is removed, the practitioner can rapidly increase compression pressure using radial artery compression device 2. By enabling rapid increase of compression pressure, radial artery compression device 2 allows the practitioner to quickly halt blood flow around the catheter and through the access site to thereby achieve hemostasis at the access site.

Figure 6:
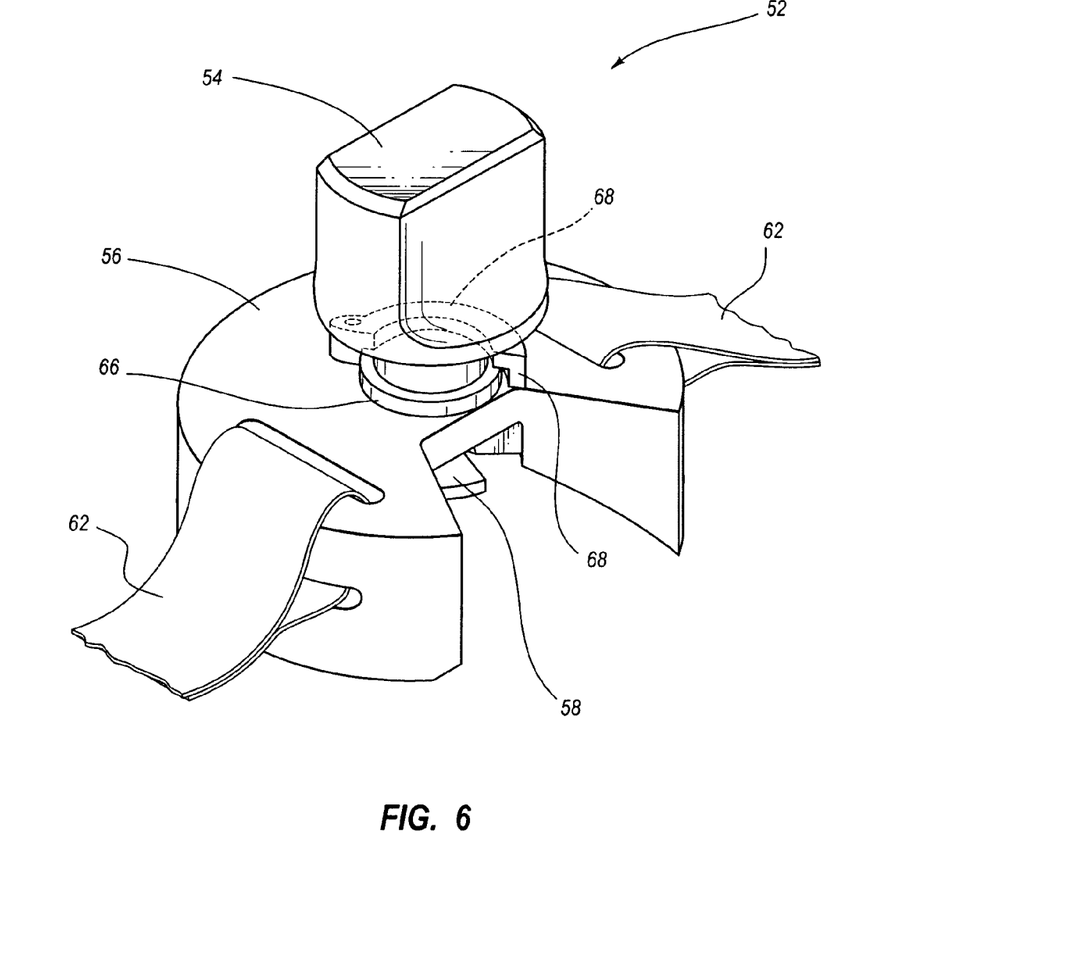
FIG. 6 is a front perspective view of an alternative embodiment of a radial artery compression device.

FIG. 6 is a front perspective view of another embodiment of a radial artery compression device 52. The illustrated embodiment, radial artery compression device 52 comprises a knob 54, a body 56, a compression pad 58, a threaded shaft 60 (see FIG. 7), and a wrist strap 62. In the illustrated embodiment, body 56 includes a retainment bracket 68, as discussed in greater detail below. Wrist strap 62 can secure radial artery compression device 52 to a wrist of a patient in a manner that positions body 56 on the underside of the wrist of the patient. The threaded shaft 60 is disposed through body 56 to mechanically couple compression pad 58 and knob 54. Threaded shaft 60 (see FIG. 7) can be integrated with knob 54, such that as knob 54 is rotated cooperative engagement with threads associated with compression pad 58 cause compression pad 58 to move relative to body 56. Depending on the direction knob 54 is rotated, compression pad 58 will extend away from body 56 or retract towards body 56. In this manner, compression pressure can be applied to the radial artery of a patient when radial artery compression device 52 is properly secured to and positioned on the patient's wrist. Moreover, the compression pressure can be increased or decreased as desired without removing radial artery compression device 52 from the wrist of the patient.

Figure 7:
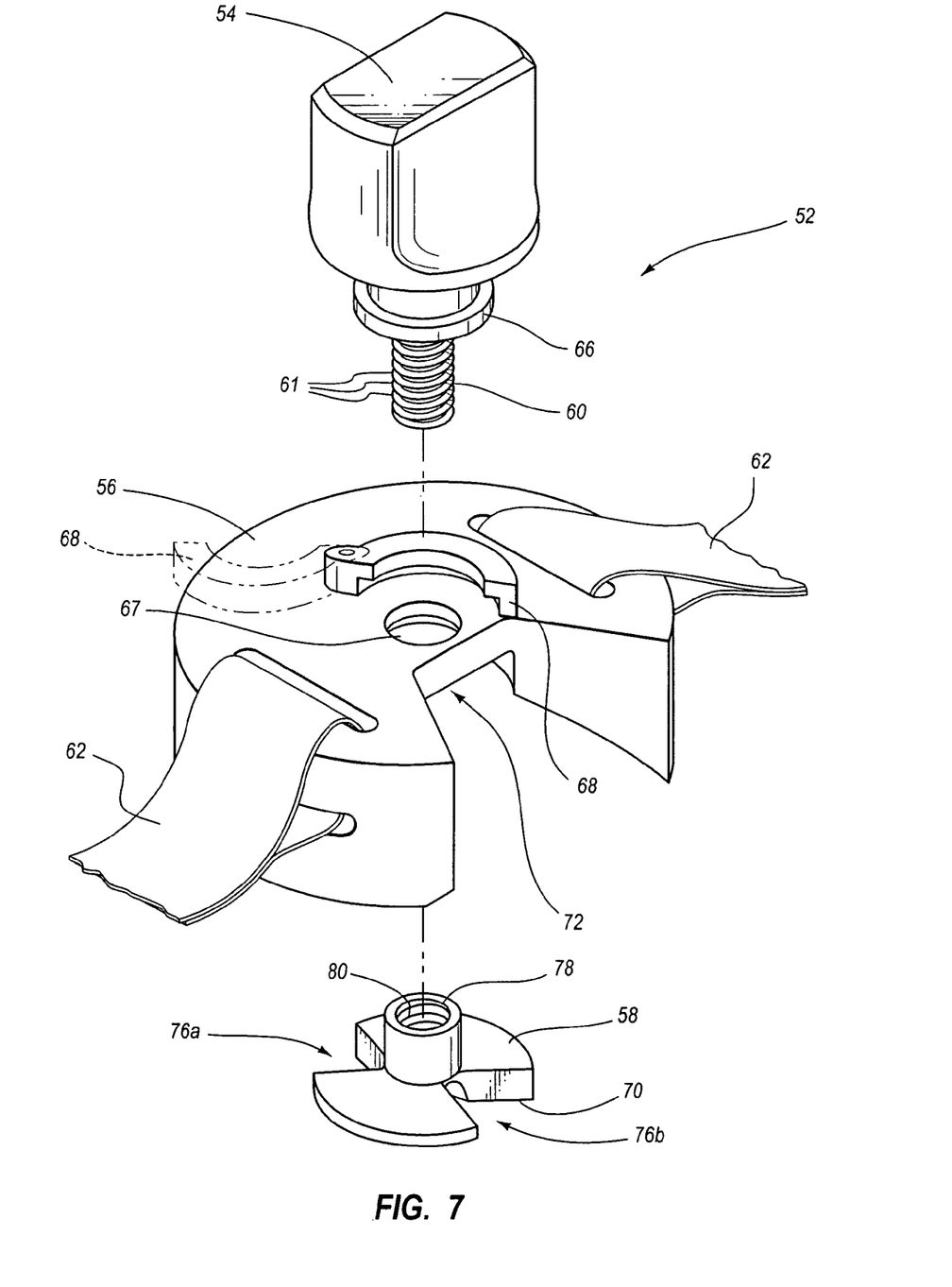
FIG. 7 is a partial exploded component view of the radial artery compression device of FIG. 6.

FIG. 7 is an exploded view of the radial artery compression device 52 of FIG. 6. In the illustrated embodiment, threaded shaft 60 can be coupled to knob 54, as depicted in FIG. 7. As knob 54 is rotated with respect to body 56, threaded shaft 60 is also rotated. Compression pad 58 includes a threaded opening 78. Threads 80 of threaded opening are configured to engage threads 61 of threaded shaft 60. As threaded shaft 60 is rotated, threads 61 of threaded shaft 60 engage the threads of threaded opening 78 and thereby bias compression pad 58 in a longitudinal direction along the axis of rotation of threaded shaft 60. In the illustrated embodiment, as knob 54 and threaded shaft 60 are rotated clockwise, compression pad 58 is retracted toward body 56. As knob 54 and threaded shaft 60 are rotated counterclockwise compression pad 58 is extended away from body 56.

The exploded view of FIG. 7 also depicts retainment bracket 68 of body 56. Retainment bracket 68 is configured to receive and secure at least a portion of knob 54 while allowing knob 54 to rotate with respect to body 56. Retainment bracket 68 is configured to engage a collar 66 of knob 54. Retainment bracket 68 pivots to allow threaded shaft 60 to be inserted through opening 67 of body 56. The positioning of threaded shaft 60 through opening 67 allows retainment bracket 68 to bias back into position such that retainment bracket 68 engages collar 66 of knob 54. Retainment bracket 68 pivots to engage collar 66 thus securing knob 54 in a fixed position relative to body 56 along the axis of rotation of knob 54. Knob 54 is free to rotate with respect to body 6 about the axis of rotation, while minimizing unintentional displacement longitudinally along the axis of rotation that would cause unintentional releasing of knob 54.

Body 56 includes a recess 72. Recess 72 is configured to receive compression pad 58 when compression pad 58 is fully retracted relative to body 56. Body 56 can be configured to contour to at least a portion of the underside of a wrist of a patient. Threaded shaft 60 is configured to be disposed through an opening 67 disposed through the middle of body 56. Threaded shaft 60 extends from knob 54 at its proximal extent distally through opening 67 of body 56. In the illustrated embodiment, the length of threaded shaft 60 is designed such that the proximal tip of threaded shaft 60 does not extend beyond the distal extent of recess 72. As a result, little or no contact is adapted to occur between compression pad 58 and a wrist of a patient when compression pad 58 is at its proximal most extent. Because threaded shaft 60 is integrally coupled to knob 54, threaded shaft 60 does not move longitudinally relative to body 56 as knob 54 is rotated. Rather, threaded shaft 60 causes compression pad 58 to move relative to body 56 as threaded shaft 60 is rotated. Threaded opening 78 of compression pad 58 is configured to enable compression pad 58 to extend beyond recess 72 permitting the application of pressure to the patient's wrist when radial artery compression device 52 is properly secured to and positioned on the wrist of a patient.

Compression pad 58 can further comprise a step 70 on the surface of compression pad 58 that is configured to be positioned proximal to a wrist of a patient. Step 70 enables compression pad 58 to at least partially contour to a portion of a sheath or catheter inserted into an access site of a radial artery of a patient and thereby enable application of compression pressure during a medical procedure to facilitate hemostasis at the access site. In the illustrated embodiment, compression pad 58 can further comprise two notches 76a and 76b positioned on opposing sides of compression pad 58. Notches 76a and 76b are configured to at least partially surround the access site of a catheter inserted into the radial artery. The configuration of notches 76 on opposing sides of compression pad 58 allows compression pad 58 to be rotated one half of a rotation to reposition step 70 relative to body 56. A half rotation may allow compression pad 58 to be repositioned with respect to the portion of the sheath or catheter inserted into the radial artery. As a result in the event that a practitioner is unable to achieve hemostasis when compression pad 58 is in a first rotational position, the practitioner can quickly reorient compression pad 58 relative to the catheter and radial artery of the patient and apply compression pressure in an attempt to achieve hemostasis. Moreover, with notches 76 positioned on opposing sides of compression pad 58, radial artery compression device 52 can easily be adapted to apply compression pressure on either the left wrist or the right wrist of a patient by simply rotating compression pad 58 to achieve a desired positioning of step 70.

A knob coupled to a threaded shaft, as depicted in FIG. 7, is an example of means for rotating a plurality of threads. A compression pad as depicted in FIG. 7 is an example of means for compressing a radial artery of a patient. A body with a retainment bracket is an example of means for supporting a rotating means and a compressing means.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A radial artery compression device, the radial artery compression device adapted to allow a user to provide varying degrees of pressurization against a patient's radial artery to maintain a desired degree of hemostasis at a percutaneous access site, the radial artery compression device comprising:
   a knob configured to be grasped by a user and rotated;
   a body configured to engage the knob such that the knob can be rotated relative to the body while remaining secured at a fixed position with respect to the body;
   a compression pad comprising;
      a first substantially planar contact surface,
      a second substantially planar contact surface, a curved step disposed between the first and second contact surfaces, the curved step comprising a single continuous radius extending from the first contact to the second contact surface, the radius of the curved step configured to contour to a radius of a device configured for insertion into the radial artery, and a notch in the perimeter of the compression pad, the notch directly intersecting the first contact surface, the second contact surface, and the radius of the curved step;

wherein the notch is in communication with the curved step such that the notch is configured to at least partially surround a device configured for insertion into the radial artery, and wherein the first and second contact surfaces are not coplanar;

a threaded shaft formed of rigid material and disposed through the body, the threaded shaft being positioned between the knob and the compression pad, the threaded shaft configured to move the compression pad with respect to the body as the knob is rotated relative to the body; and a band to secure the body to the underside of a wrist of a patient in the area of the radial artery, such that the compression pad can be positioned adjacent the wrist of the patient wherein the user rotates the knob to selectively move the compression pad between a first position and at least a second position to provide varying degrees of pressurization to the wrist of a patient, wherein when the compression pad is in a first position, the compression pad is positioned adjacent the body and applies a lesser degree of pressurization against the wrist of the patient and when the compression pad is in the second position, the compression pad is positioned a given amount of displacement from the body and provides a greater amount of pressurization against the patient's wrist;

wherein the knob comprises threads to engage threads on the threaded shaft such that rotation of the knob moves the shaft with respect to the body.

2. The radial artery compression device of claim 1, wherein the threaded shaft is integrated with the compression pad.

3. The radial artery compression device of claim 2, wherein clockwise rotation of the knob moves the shaft and the compression pad toward the body to a retracted position and counterclockwise rotation of the knob extends the shaft and compression pad away from the body and toward the wrist and radial artery of the patient.

4. The radial artery compression device of claim 1, wherein when the device is secured to the underside of the wrist of a patient, as the knob is rotated to cause the compression pad to extend away from the body and toward the wrist and radial artery of the patient, the compression pad gradually applies pressure to the radial artery of the patient.

5. The radial artery compression device of claim 4, wherein the compression pad is configured to apply pressure to the radial artery in a manner that prevents blood from flowing out through an opening in the radial artery to thereby achieve hemostasis at the opening.

6. The radial artery compression device of claim 5, wherein the compression pad is configured to apply pressure to the radial artery while a sheath is inserted through the opening to perform a medical procedure, wherein the pressure can be applied in a manner that prevents blood from flowing around the sheath and out the opening to thereby achieve hemostasis at the opening.

7. The radial artery compression device of claim 5, wherein the compression pad is configured to apply pressure to the radial artery while a catheter is inserted through the opening to perform a medical procedure, wherein the pressure can be applied in a manner that prevents blood from flowing around the catheter and out the opening to thereby achieve hemostasis at the opening.

8. The radial artery compression device of claim 1, wherein the body is configured such that at least a portion of the body is contoured to at least a portion of the underside of the wrist of the patient.

9. The radial artery compression device of claim 1, wherein the knob comprises a collar, and wherein the body engages the knob by engaging the collar of the knob.

10. The radial artery compression device of claim 9, wherein the body further comprises a pivotable retainment bracket to engage the collar of the knob.

11. The radial artery compression device of claim 1, wherein the compression pad is a disk shaped.

12. The radial artery compression device of claim 11, wherein the curved step is configured to enable the compression pad to at least partially contour to a portion of a device within the radial artery during a medical procedure.

13. The radial artery compression device of claim 1, wherein the body further comprises a recess configured to receive the compression pad when the compression pad is fully retracted toward the body.

14. A method for achieving hemostasis at an access site of a radial artery of a patient, the method comprising:
    providing a radial artery compression device comprising,
        a knob configured to be grasped by a user and rotated,
        a body configured to engage the knob such that the knob can be rotated relative to the body while remaining secured at a fixed position with respect to the body,
        a compression pad comprising:
            a first substantially planar contact surface,
            a second substantially planar contact surface,
            a curved step disposed between the first and second contact surfaces, the curved step comprising a single continuous radius extending from the first contact to the second contact surface, the radius of the curved step configured to contour to a radius of a device configured for insertion into the radial artery, and
            a notch in the perimeter of the compression pad, the notch directly intersecting the first contact surface, the second contact surface, and the radius of the curved step;
            wherein the notch is in communication with the curved step such that the notch is configured to at least partially surround a device configured for insertion into the radial artery, and
            wherein the first and second contact surfaces are not coplanar;
        a threaded shaft formed of rigid material and disposed through the body and between the knob and the compression pad, the threaded shaft configured to move the compression pad with respect to the body as the knob is rotated relative to the body, and
        a band to secure the body to the underside of a wrist of the patient in the area of the radial artery, such that the compression pad is positioned adjacent the wrist of the patient;
    securing the radial artery compression device to a wrist of the patient, the compression pad of the radial artery compression device positioned adjacent the access site of the radial artery of the patient; and rotating the knob relative to the body to increase compression pressure applied by the compression pad at the access site until hemostasis at the access site is achieved, wherein the knob comprises threads to engage threads on the threaded shaft such that rotation of the knob moves the shaft with respect to the body.

15. The method of claim 14, wherein a device is inserted into the radial artery via the access site, wherein the compression pad of the radial artery compression device includes at least one notch configured to at least partially surround the inserted device at the access site, and wherein the method further comprises positioning the notch of the compression pad to partially surround the inserted device.

16. The method of claim 14, wherein a device is inserted into the radial artery via the access site, wherein the curved step is configured to at least partially contour to a portion of the inserted device within a radial artery of a patient, and wherein the method further comprises positioning the step of the compression pad to align with the inserted portion of the device.

17. A radial artery compression device, comprising:
  means for rotating a first plurality of threads, the rotating means configured to be grasped by a user and rotated;
  a compression pad comprising;
    a second plurality of threads,
    a first substantially planar contact surface,
    a second substantially planar contact surface,
    a curved step disposed between the first and second contact surfaces, the curved step comprising a single continuous radius extending from the first contact to the second contact surface, the radius of the curved step configured to contour to a radius of a device configured for insertion into the radial artery, and
    a notch in the perimeter of the compression pad, the notch directly intersecting the first contact surface, the second contact surface, and the radius of the curved step;
  wherein the notch is in communication with the curved step such that the notch is configured to at least partially surround a device configured for insertion into the radial artery, and wherein the first and second contact surfaces are not coplanar, the compression pad configured such that the first plurality of threads engages the second plurality of threads, wherein rotation of the rotating means displaces the compression pad longitudinally along an axis of rotation of the rotating means to adjust the level of compression pressure applied to the radial artery of the patient;
  means for supporting the rotating means and the compression pad, the supporting means configured to engage the rotating means such that the rotating means can be rotated relative to the supporting means while remaining secured at a fixed position with respect to the supporting means and the supporting means configured to receive the compression pad when the compression pad is displaced longitudinally toward the supporting means along the axis of rotation of the rotating means; and
  means for securing the supporting means to the underside of a wrist of a patient in the area of the radial artery, such that the compression pad is positioned adjacent the wrist of the patient.

18. The radial artery compression device of claim 17, wherein the compression pad is configured to at least partially surround a device inserted into the radial artery of the patient.

19. The radial artery compression device of claim 17, wherein the compression pad includes means for at least partially contouring to a device inserted into the radial artery of the patient, wherein the contouring means is configured to at least partially contour to a portion of the device within the radial artery when the compression pad is compressing a radial artery of the patient.

* * * * *